(12) United States Patent
Florio et al.

(10) Patent No.: US 6,904,317 B2
(45) Date of Patent: Jun. 7, 2005

(54) METHOD AND APPARATUS FOR DYNAMICALLY ADJUSTING OVERDRIVE PACING PARAMETERS

(75) Inventors: Joseph J. Florio, La Canada, CA (US); Gene A. Bornzin, Simi Valley, CA (US); Peter Boileau, Valencia, CA (US); Eric Falkenberg, Simi Valley, CA (US); Janice Barstad, Maple Grove, MN (US)

(73) Assignee: Pacesetter, Inc., Sylmar, CA (US)

( * ) Notice: Subject to any disclaimer, the term of this patent is extended or adjusted under 35 U.S.C. 154(b) by 486 days.

(21) Appl. No.: 10/043,472

(22) Filed: Jan. 9, 2002

(65) Prior Publication Data

US 2003/0130703 A1 Jul. 10, 2003

(51) Int. Cl.[7] .................................................. A61N 1/36
(52) U.S. Cl. ............................................. 607/9; 607/11
(58) Field of Search .............................. 607/9, 4, 5, 14, 607/11, 27, 32

(56) References Cited

U.S. PATENT DOCUMENTS

| | | | |
|---|---|---|---|
| 4,712,555 A | 12/1987 | Thornander et al. | 128/419 PG |
| 4,940,052 A | 7/1990 | Mann et al. | 128/419 PG |
| 4,944,298 A | 7/1990 | Sholder | 128/419 PG |
| 5,466,254 A | 11/1995 | Helland | 607/123 |
| 6,058,328 A | 5/2000 | Levine et al. | 607/14 |
| 6,167,308 A | 12/2000 | DeGroot | 607/14 |
| 6,185,459 B1 | 2/2001 | Mehra et al. | 607/14 |
| 6,606,517 B1 * | 8/2003 | Park et al. | 607/14 |
| 2001/0007948 A1 | 7/2001 | Stoop et al. | 607/14 |

* cited by examiner

*Primary Examiner*—Angela D. Sykes
*Assistant Examiner*—Roderick Bradford

(57) ABSTRACT

Dynamic overdrive pacing adjustment techniques are described for use in implantable cardiac stimulation devices. In a first technique, an overdrive pacing unit of a microcontroller of the implantable device operates to optimize various control parameters that affect overdrive pacing so as to achieve a desired degree of overdrive pacing for the particular patient in which the stimulation device is implanted. Parameters to be optimized include the number of overdrive beats paced once overdrive pacing is trigged, the overdrive pacing response function, the recovery rate, and various base rates. The control parameters are adjusted in a hierarchical order of priority until the desired degree of overdrive pacing is achieved. Adjustment of the number of overdrive beats, the recovery rate, and various base rates is iteratively performed by using incremental numerical adjustments. Adjustment of the overdrive pacing response function may be performed by selecting among a set of fixed predetermined linear response functions. In a second technique, the overdrive pacing unit operates to optimize the shape of a single non-linear dynamic overdrive pacing response function so as to achieve the desired degree of overdrive pacing for the patient. The second technique may either be employed alone or in combination with the first, hierarchical optimization technique.

24 Claims, 7 Drawing Sheets

METHOD AND APPARATUS FOR DYNAMICALLY ADJUSTING OVERDRIVE PACING PARAMETERS

FIELD OF THE INVENTION

The invention generally relates to implantable cardiac stimulation devices such as pacemakers or implantable cardioverter defibrillators (ICDs), and in particular, to techniques for overdrive pacing heart tissue to prevent or terminate arrhythmias.

BACKGROUND OF THE INVENTION

An arrhythmia is an abnormal heartbeat pattern. One example of arrhythmia is bradycardia wherein the heart beats at an abnormally slow rate or wherein significant pauses occur between consecutive beats. Another example is a tachycardia wherein the heart beats at an abnormally fast rate. With atrial tachycardia, the atria of the heartbeat abnormally fast. With ventricular tachycardia, the ventricles of the heart beat abnormally fast. Though often unpleasant for the patient, a tachycardia is typically not fatal. However, some tachycardias, particularly ventricular tachycardia, can trigger ventricular fibrillation wherein the heart beats chaotically, such that there is little or no net flow of blood from the heart to the brain and other organs. Ventricular fibrillation, if not terminated, is fatal. Hence, it is highly desirable to prevent or terminate arrhythmias, particularly arrhythmias of the type that may lead to ventricular fibrillation.

One technique for preventing or terminating arrhythmias is overdrive pacing wherein the implantable cardiac stimulation device applies electrical pacing pulses to the heart at a rate somewhat faster than the natural or "intrinsic" heart rate of the patient. Overdrive pacing for prevention of tachyarrhythmias is also taught in U.S. Pat. No. 6,058,328 by Levine et al. and in U.S. patent application Ser. No. 09/471,788 by Florio et al. For bradycardia, the cardiac stimulation device may be programmed to artificially pace the heart at a rate of 60 to 80 pulses per minute (ppm) to thereby prevent the heart from beating too slow and to eliminate any long pauses between heartbeats. To prevent a tachycardia from occurring, the cardiac stimulation device artificially paces the heart at a rate of at least five to ten beats per minute faster than the intrinsic heart rate of the patient. In other words, a slight artificial tachycardia is induced and maintained in an effort to prevent an actual tachycardia from arising. If an actual tachycardia occurs, such as a supraventricular tachycardia (SVT) wherein the heart may begin beating suddenly at 150 beats per minute (bpm) or more, the cardiac stimulation device senses the tachycardia and immediately begins pacing at a rate of at least five to ten ppm faster than the tachycardia, then slowly decreases the pacing rate in an attempt to slowly reduce the heart rate back to a normal rate thereby terminating the tachycardia.

It is believed that overdrive pacing is effective for at least some patients for preventing or terminating the onset of tachycardia for the following reasons. A normal, healthy heart beats only in response to electrical pulses generated from a portion of the heart referred to as the sinus node. The sinus node pulses are conducted to the various atria and ventricles of the heart via certain, normal conduction pathways. In some patients, however, additional portions of the heart also generate electrical pulses referred to as "ectopic" pulses. Each pulse, whether a sinus node pulse or an ectopic pulse has a refractory period subsequent thereto during which time the heart tissue is not responsive to any electrical pulses. A combination of sinus pulses and ectopic pulses can result in a dispersion of the refractory periods, which, in turn, can trigger a tachycardia. By overdrive pacing the heart at a uniform rate, the likelihood of the occurrence of ectopic pulses is reduced and the refractory periods within the heart tissue are thereby rendered more uniform and periodic. Thus, the dispersion of refractory periods is reduced and tachycardias are substantially avoided. If a tachycardia nevertheless occurs, overdrive pacing at a rate faster than a tachycardia helps to eliminate any ectopic pulses that may be occurring and thereby helps terminate the tachycardia.

Thus it is desirable within patients prone to tachycardia to ensure that most beats of the heart are paced beats, as any unpaced beats may be ectopic beats. A high percentage of paced beats can be achieved simply by establishing a high overdrive pacing rate. However, a high overdrive pacing rate has disadvantages as well. A high overdrive pacing rate may be unpleasant to the patient, particularly if the artificially-induced heart rate is relatively high in comparison with the heart rate that would otherwise normally occur. A high overdrive pacing rate may also cause possible damage to the heart or may trigger more serious arrhythmias, such as a ventricular fibrillation. A high overdrive rate may be especially problematic in patients suffering from heart failure, particularly if the heart failure is due to an impaired diastolic function. Indeed, a high overdrive rate may actually exacerbate heart failure in these patients. Also, a high overdrive rate may present a problem in patients with coronary artery disease because increasing the heart rate decreases diastolic time and decreases perfusion, thus intensifying ischemia. Also, the need to apply overdrive pacing pulses operates to deplete the power supply of the stimulation device, perhaps necessitating surgical replacement of the stimulation device.

Accordingly, it is desirable to provide a degree of overdrive pacing that is high enough to eliminate tachycardias, but not so high as to pose other risks. For many patients, the optimal degree of overdrive pacing as measured by the percentage of paced beats out of total heartbeats is between 85% and 95%. In other words, out of every twenty heartbeats, only two or three beats should be intrinsic beats, the rest should be paced beats. The degree of overdrive pacing is affected by a number of programmable control parameters, which the physician adjusts using an external programming device in an attempt to achieve the desired degree of overdrive pacing. Among the parameters that affect the degree of overdrive pacing are 1) the overdrive pacing response function or response "slope"; 2) the number of overdrive events; 3) the recovery rate; 4) the base rate; 5) the rest rate; and 6) the circadian base rate. Briefly, the overdrive pacing response function specifies an overdrive pacing rate to be applied when overdrive pacing is triggered with the overdrive pacing rate dependent upon the heart rate in effect when overdrive pacing is triggered. Overdrive pacing is triggered, for example, upon the detection of two intrinsic heartbeats out of the last sixteen paced or intrinsic beats. The number of overdrive events specifies the number of consecutive beats to be paced following triggering of overdrive pacing. The number of overdrive events may be a function of heart rate in effect when overdrive pacing is triggered, or may be one value, which applies to all rates. The recovery rate specifies a rate decrement by which the pacing rate is to be decreased after the number of overdrive events, have been paced. The base rate specifies a standard non-overdrive pacing rate for use while the patient is awake. The rest rate specifies an alternative non-overdrive base rate for use while the patient is asleep or otherwise at profound rest. The circadian base rate is yet an alternative base rate which maybe used instead of the standard base rate and rest rate. The circadian base rate is typically set equal to the average active heart rate while the patient is awake and set equal to the average rest heart rate while the patient is at rest.

With regard to the overdrive pacing response functions, typically one or more overdrive pacing response function is pre-programmed into the stimulation device. Each specifies an overdrive pacing rate for each corresponding intrinsic heart rate throughout a broad range of detectable heart rates, such as from 55 bpm to 150 bpm. FIG. 1 illustrates an exemplary set of three response functions or slopes each of which specifies an overdrive pacing rate (shown on the y-axis) as a function of the intrinsic atrial rate (shown on the x-axis). The intrinsic atrial is rate is shown in bold. Briefly, the physician programming the stimulation device selects one of the response functions. Thereafter, the stimulation device detects the intrinsic heart rate then determines the overdrive pacing rate corresponding to the intrinsic rate by examining the selected response function then paces the heart at that rate. If response function #1 has been selected and the intrinsic rate is 70 bpm, an overdrive pacing rate of 75 ppm is specified by the response function and the heart is overdrive paced at that rate. If response function #2 has been selected and the intrinsic rate is 70 bpm, an overdrive pacing rate of 80 ppm and the heart is overdrive paced at that rate. The higher the overdrive rate as compared to the intrinsic rate, the more aggressive the overdrive pacing. By providing multiple response functions, the physician can thereby set the aggressiveness of overdrive pacing. (Typically, a half dozen or more response functions are provided. For clarity in illustrating the response functions, only three are shown in the figure.) Note however that the predetermined response functions are generally linear, i.e. for most response functions the differences between the overdrive pacing rate and the current heart rate is fairly uniform throughout the entire range of detectable heart rates. Considering response function #1, regardless of whether the current heart rate is 55 bpm or 150 bpm, the overdrive rate is 5 ppm higher. For some response functions, such as response function #3, the overdrive pacing increase over the heart rate is somewhat less for high heart rates than for low heart rates, but the difference from high to low changes fairly gradually and uniformly over the full range of heart rates. As a result of this general "linearity" of the response functions, the selection of a different response function usually results in a fairly uniform increase or decrease in all overdrive pacing rates for all ranges of heart rates.

In use, the stimulation device monitors the heart of the patient and, if a predetermined intrinsic rate is detected, overdrive pacing is automatically triggered. The overdrive pacing rate is determined using the selected response function and the heart rate at the time overdrive is triggered. The stimulation device then overdrive paces the heart at the selected overdrive pacing rate for the programmed number of overdrive events. Thereafter, the stimulation device slowly decreases the overdrive pacing rate by the rate decrement specified by the programmed recovery rate until additional intrinsic beats are detected, then the device repeats the process to determine a new overdrive pacing rate and paces accordingly. If the heart rate is increasing quickly, such as may occur with an episode of tachycardia, the stimulation device may still detect intrinsic beats even while overdrive pacing is being applied. If so, the stimulation device immediately determines a new higher overdrive pacing rate based on the selected response function and the new heart rate. Again, if intrinsic beats are still detected, the overdrive pacing rate is increased per the response function. In this manner, the overdrive pacing rate may quickly be increased to 150 ppm or more in response to a tachycardia such as SVT.

Ultimately, the overdrive rate will be increased to the point where it exceeds the intrinsic rate of the tachycardia and hence no intrinsic beats will be detected. The pacing rate is eventually decreased using the recovery rate until two intrinsic beats out of sixteen cycles are again detected and the pacing rate is increased again. Assuming that overdrive pacing has succeeded in terminating the tachycardia, the recovery rate will ensure that the pacing rate decreases slowly back down to a normal rate of perhaps 60 to 80 bpm. If a base rate is programmed, such as 60 bpm, the heart will be paced at the base rate even if the recovery rate would otherwise cause the rate to decrease even further. Likewise, if an alternative base rate, such as the rest rate or circadian base rate are programmed, the pacing rate will not fall below those rates either.

With this technique, so long as the intrinsic rate remains above the currently programmed base rate then, regardless of whether the intrinsic heart rate remains stable or increases or decreases rapidly, the heart is overdrive paced so that the actual heart rate of the patient remains above the intrinsic heart rate most of the time, with only occasional intrinsic heartbeats. When employing this technique, the resulting degree of overdrive pacing is a complicated function of the various programmable control parameters and of the characteristics of the heart of the patient, such as whether the patient is prone to tachyarrhythmia or bradycardia. Generally, the more aggressive the response function, the higher the degree of overdrive pacing. The more aggressive the recovery rate, the lower the degree of overdrive pacing. The greater the number of overdrive events in each sequence of overdrive pacing, the greater the degree of overdrive pacing. The higher the base rate, rest rate or circadian base rate, the higher the degree of overdrive pacing. If the patient is prone to frequent tachycardias, the degree of overdrive pacing is typically lower than otherwise. If the patient is prone to frequent bradycardia, the degree of overdrive pacing is typically higher than otherwise.

The various parameters affecting the degree of overdrive pacing are programmed by the physician in an attempt to ensure that the optimal degree of overdrive pacing is achieved of typically 85% to 95%. Unfortunately, it is quite difficult for a physician to initially determine the parameters needed to achieve the desired degree of overdrive pacing within a particular patient. Instead, the physician typically sets the various control parameters of the stimulation device of the patient to default values and then programs the device to record the resulting degree of overdrive pacing as a function of heart rate. The patient is sent home and, weeks or months later, the patient returns to the physician for a follow-up session to permit the physician to review the recorded information and to determine whether the default parameters achieved the desired degree of overdrive pacing. If the degree of overdrive pacing is too low, perhaps only 50%, the physician typically increases the number of overdrive events or selects a more aggressive response function. If the degree of overdrive pacing is too high, perhaps 100%, the physician decreases the number of overdrive events or selects a less aggressive response function. The patient is again sent home and, weeks or months later, the patient again returns to the physician so that the physician can again review the recorded degree of overdrive pacing and, if needed, re-set the number of overdrive events or the response function. This process is usually repeated several times over a period of many months until a number of overdrive events and a response function are identified that comes closest to achieving the desired degree of overdrive pacing. During this process the physician may also adjust any of the other parameters as well, such as the base rate, recovery rate etc.

As can be appreciated, the need for frequent follow-up sessions can be a considerable inconvenience to the patient and can increase overall health care costs. Also, during the potentially lengthy period of time before the control parameters are optimized, the degree of overdrive pacing is either too low or too high posing the aforementioned risks.

Accordingly, it would be highly desirable to provide an improved overdrive pacing technique permitting the desired degree of overdrive pacing to be more expediently achieved without the need for frequent follow-up sessions between patient and physician and it is to this end that aspects of the invention are directed.

Moreover, because the stimulation device has only a limited set of preprogrammed response functions, the best response function may not achieve the desired degree of overdrive pacing. A significant problem is this regard is that the predetermined response functions are substantially linear and hence the selection of a different response function usually results in only a uniform increase or decrease in all overdrive pacing rates for all ranges of heart rates. Hence, at best, the physician may only be able to achieve the desired degree of overdrive pacing for certain ranges of heart rates, such as low heart rates or high heart rates, but not for all heart rates. As a result, the best response function may achieve an overall degree of overdrive pacing of, for example, only 75%. Thus, with conventional overdrive pacing techniques, the desired degree of overdrive pacing sometimes simply cannot be achieved despite repeated follow-up sessions with the physician and despite modifying any or all of the programmable parameters.

Accordingly, it also would be highly desirable to provide an improved technique permitting the desired degree of overdrive pacing to be more precisely achieved and in particular for overcoming the disadvantages associated with fixed, predetermined response functions, and it is to this end that other aspects of the invention are directed.

SUMMARY OF THE INVENTION

A system and method are provided for use within an implantable cardiac stimulation device for automatically and dynamically optimizing the shape of an overdrive pacing response function. In accordance with the method, an initial shape of the overdrive pacing response function is selected and the heart is paced by applying the response function to determine an overdrive pacing rate whenever an event triggering overdrive pacing is detected. The degree of overdrive pacing achieved using the response function is determined and then the shape of the response function is automatically adjusted to vary the degree of overdrive pacing in an attempt to subsequently achieve a selected degree of overdrive pacing, such as 85% to 95%.

Thus, the shape of a single non-linear overdrive pacing response function is automatically and dynamically adjusted so as to achieve the desired degree of overdrive pacing. This is in contrast with conventional techniques of the type described above wherein, to adjust the degree of overdrive pacing, a physician manually selects among a set of fixed, predetermined response functions during a follow-up session with the patient. As noted above, with such systems, the predetermined response functions are often substantially linear and hence the selection of a different response function usually results in an increase or decrease in all overdrive pacing rates for all ranges of heart rates. With the nonlinear response function of the invention, the shape of the overdrive response function is automatically changed, as needed, to increase the overdrive rate for some heart rates and to decrease the overdrive rate for other heart rates so as to optimize the response function and achieve the desired degree of overdrive pacing. As a result, the desired degree of overdrive pacing typically can be much more quickly and precisely achieved than with techniques wherein the physician can only select among predetermined response functions. Moreover, because the response function is automatically adjusted, frequent follow-up sessions between patient and physician are typically not required. Other objects, features and advantages of the invention are described below.

In an exemplary embodiment, the response function specifies an overdrive pacing rate corresponding to each detected heart rate throughout a range of detectable heart rates, with each overdrive pacing rate being greater than or equal to the corresponding detected heart rate. The degree of overdrive pacing achieved using the selected response function is determined by tracking the heart rate over a period of 24 to 48 hours. For each of a set of predetermined ranges of heart rates, an overdrive pacing percentage is determined. The non-linear response function is then automatically and dynamically adjusted to achieve the selected degree of overdrive pacing by specifying an optimal range of overdrive pacing percentages for each of the predetermined ranges of heart rates and comparing the detected overdrive percentage with the optimal overdrive percentage for each of the ranges of heart rates. If the detected overdrive percentage exceeds the optimal overdrive percentage for a particular range of heart rates, the overdrive pacing rate of the response function corresponding to the particular range of heart rates is decreased. Otherwise, the overdrive pacing rate of the response function corresponding to the heart rates of the range of heart rates is increased.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 2:
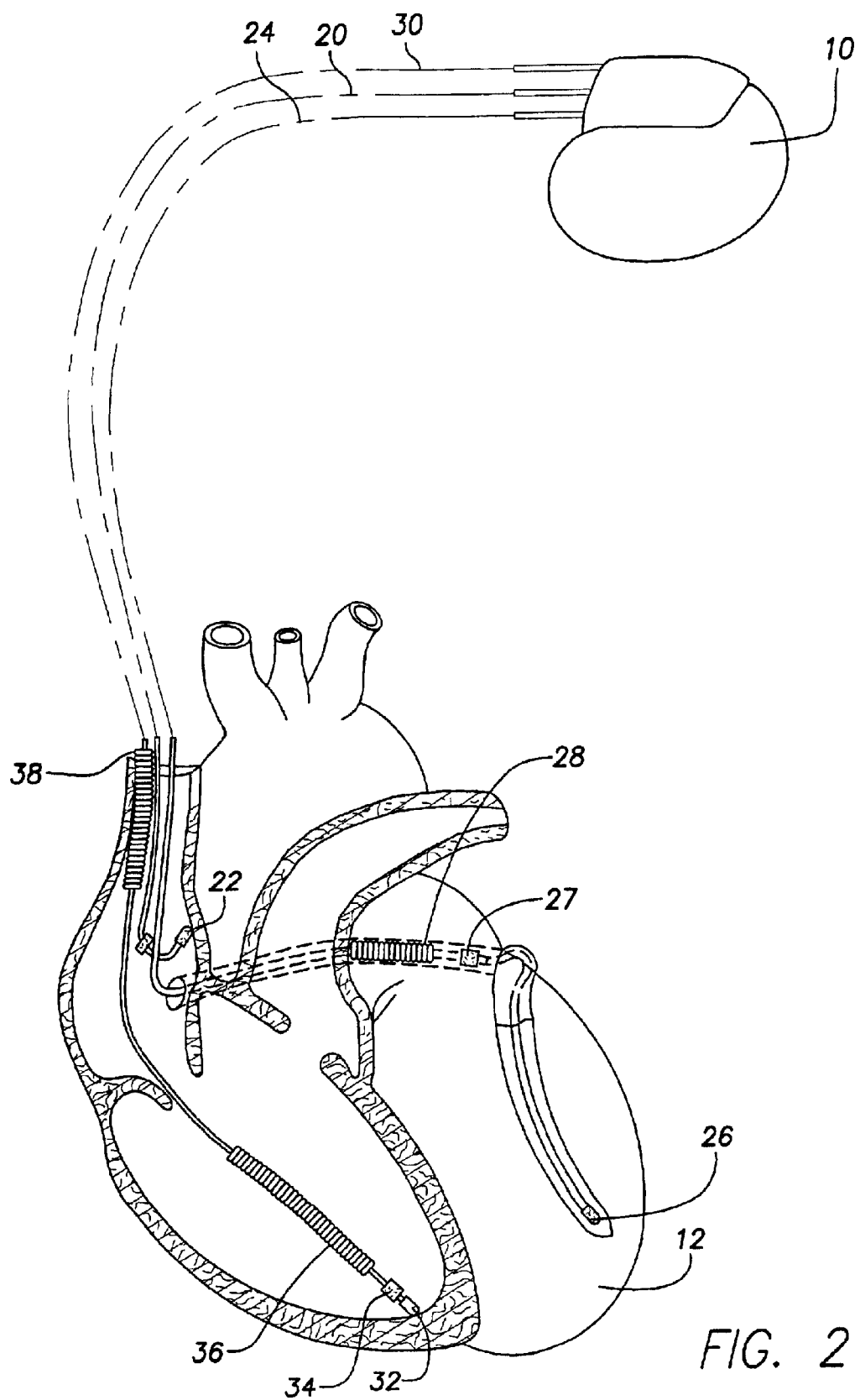
FIG. 2 is a simplified diagram illustrating an implantable stimulation device in electrical communication with at least three leads implanted into the heart of a patient for delivering multi-chamber stimulation and shock therapy and configured in accordance with the invention to perform overdrive pacing.

As shown in FIG. 2, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 3:
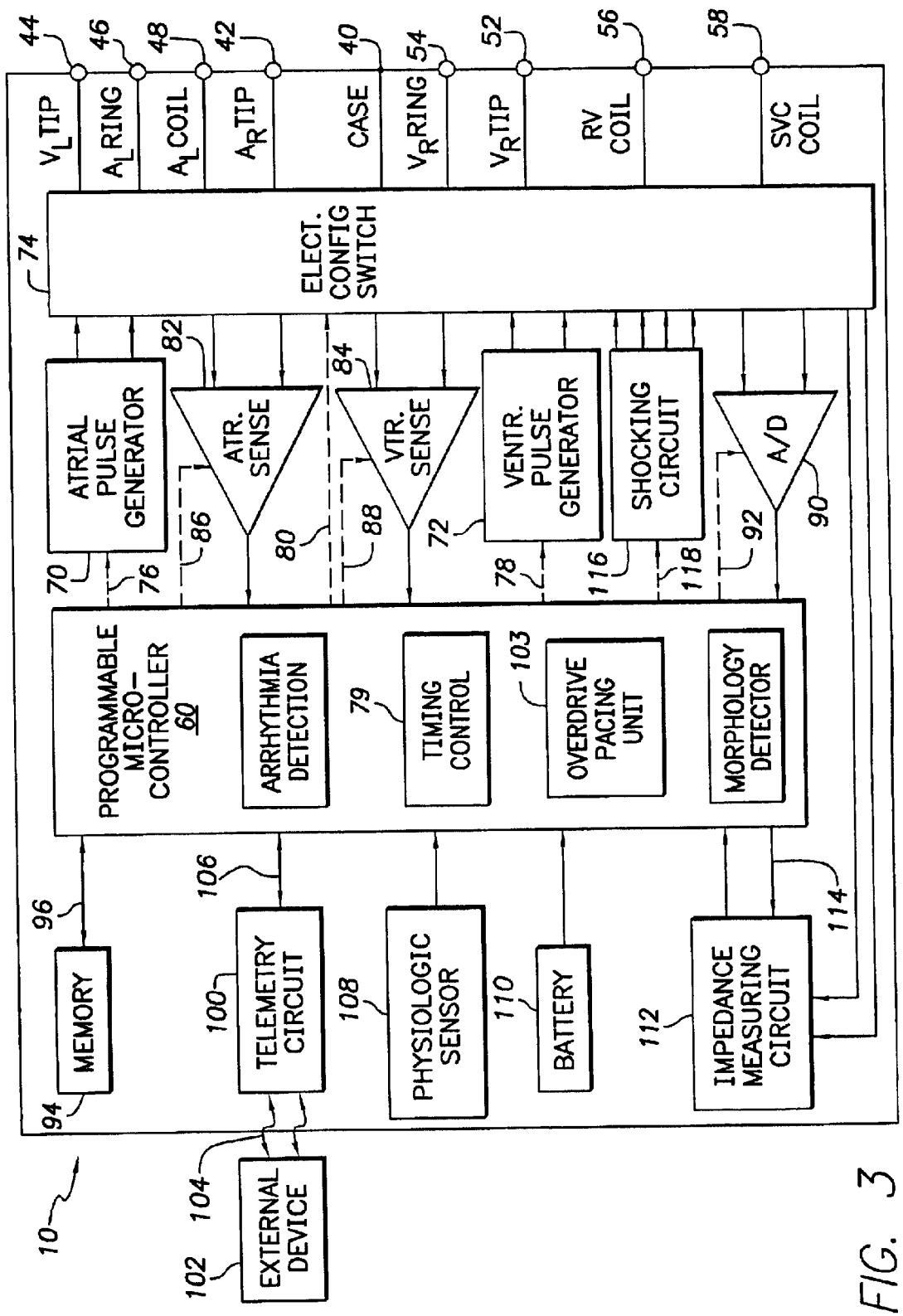
FIG. 3 is a functional block diagram of the implantable cardiac stimulation device of FIG. 2 illustrating basic elements of a stimulation device.

As illustrated in FIG. 3, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 3, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art. Representative types of control circuitry that may be used with the invention include the microprocessor-based control system of U.S. Pat. No. 4,940,052 (Mann et al.), the state-machine of U.S. Pat. Nos. 4,712,555 (Sholder) and 4,944,298 (Sholder).

As shown in FIG. 3, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

The microcontroller includes an overdrive pacing unit 103 for controlling overdrive pacing based on a set of additional control parameters including the overdrive pacing response function, the number of overdrive events; and the recovery rate. The overdrive pacing response function specifies the overdrive pacing rate to be applied when overdrive pacing is triggered as a function of the heart rate when overdrive pacing is triggered. Overdrive pacing is triggered upon the detection of X intrinsic heartbeats out of Y pacing cycles, where a pacing cycle may be defined as any intrinsic OR paced heartbeat. Preferred values of X and Y are 2 and 16 respectively. The number of overdrive events specifies the number of consecutive beats to be paced following triggering of a sequence of overdrive pacing beats. The number of overdrive events may be a single number for all heart rates, or may be a function of the heart rate when overdrive pacing is triggered. The recovery rate specifies a rate decrement by which the overdrive pacing rate is to be decreased after the number of overdrive events have been paced.

In use, overdrive pacing unit 103 monitors heartbeats of the patient and, if X intrinsic heartbeats are detected out of Y pacing cycles, overdrive pacing is triggered. The overdrive pacing rate is determined using the overdrive pacing response function and the heart rate detected at the time overdrive is triggered. Overdrive pacing unit 103 overdrive paces the heart at the selected overdrive pacing rate for a programmed number of overdrive events. Thereafter, overdrive pacing unit 103 slowly decreases the overdrive pacing rate by a rate decrement specified by the programmed recovery rate until X intrinsic beats out of Y pacing cycles are again detected, then the overdrive pacing unit repeats the process to determine a new overdrive pacing rate and paces accordingly. If a base rate is programmed, such as 60 bpm, the heart will be paced at the base rate even if the recovery rate would otherwise cause the rate to decrease even further. Likewise, if an alternative base rate, such as the rest rate or circadian base rate are programmed, the pacing rate will not fall below those rates either.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. The type of sensor used is not critical to the invention and is shown only for completeness.

The stimulation device additionally includes a battery 110, which provides operating power to all of the circuits shown in FIG. 3. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 3, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

With reference to the remaining figures, first and second embodiments of the dynamic overdrive pacing adjustment techniques of the invention will be described. In the first embodiment, described primarily with reference to FIGS. 4–5, the overdrive pacing unit of the microcontroller of the stimulation device operates to optimize control parameters that affect overdrive pacing so as to achieve a desired degree of overdrive pacing for the particular patient in which the stimulation device is implanted. One of the parameters optimized is an overdrive pacing response function, which may either be a substantially linear response function selected from a set of predetermined fixed response functions or may be a non-linear response function having a shape that can be dynamically adjusted. In the second embodiment, described primarily with reference to FIGS. 6–9, the overdrive pacing unit 103 operates to optimize the shape of the non-linear overdrive pacing response function so as to achieve the desired degree of overdrive pacing for the patient. The technique of FIGS. 6–9 may either be employed alone or as a portion of the more general optimization techniques of FIGS. 4–5.

Figure 4:
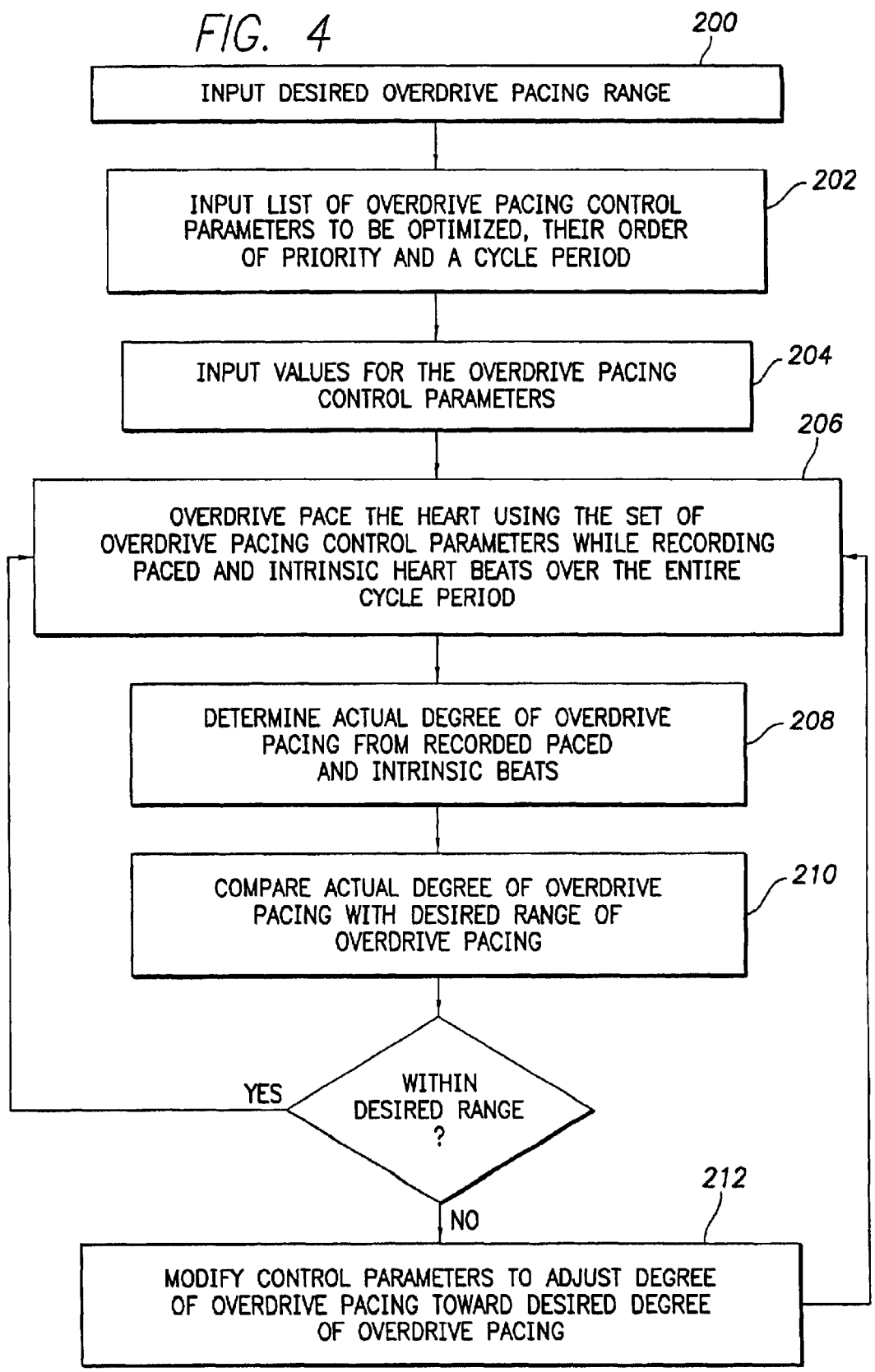
FIG. 4 is a flow chart providing an overview of the operation of a first embodiment of the invention wherein the implantable stimulation device automatically adjusts a set of overdrive pacing control parameters so as to achieve a desired degree of overdrive pacing.

Referring first to FIG. 4, a flow chart is shown describing an overview of the operation and novel features of stimulation device 10 as configured in accordance with the first embodiment of the invention. In this flow chart, and the other flow charts described herein, the various algorithmic steps are summarized in individual "blocks". Such blocks describe specific actions or decisions made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

At step 200, overdrive pacing unit 103 of microcontroller 60 (FIG. 3) inputs a desired overdrive pacing range which may be, for example, 85% to 95% as measured as the number of paced beats out of total number of paced and intrinsic beats. It will be apparent that other ranges may be used as well, or that simply a lower threshold may be set (e.g., at least 85%). The range is initially programmed by a physician and stored in memory 94 (also FIG. 3). If no range is provided by the physician a default range programmed by the manufactured is employed. At step 202, the overdrive pacing unit inputs a list of parameters affecting overdrive pacing functions to be optimized, the hierarchical order by which the parameters are to be optimized, and a cycle period specifying how frequently the parameters are to be automatically adjusted for the purposes of optimization, typically 24 or 48 hours. At step 204, a set of initial values for the control parameters are input. The list of parameters and their initial values are also both programmed by the physician and stored in memory and, if not provided by the physician, default parameters provided by the manufactured are used.

An exemplary list of control parameters and initial values input at steps 202 and 204 in the order of optimization is:

1) Number of Overdrive Events

The number of paced beats at the overdrive pacing rate which follow detection of intrinsic activity (i.e. 2 intrinsic beats detected out of the last 16 cycles) before the recovery rate is applied.

Initial value: 16;

2) Overdrive Pacing Response Function

Specifies the particular overdrive pacing rate to be applied at each detected heart rate when overdrive pacing is triggered.

Initial value: response function #1 specifying an overdrive rate of 5 ppm above the detected rate for all heart rates;

3) Recovery Rate

The rate decrement by which the pacing rate is decreased subsequent to completion of the number of overdrive events.

Initial value: 1 bpm per paced beat;

4) Base Rate

The standard non-overdrive pacing rate for use while the patient is awake.

Initial value: 80 bpm;

5) Rest Rate

The non-overdrive base rate for use while the patient is at profound rest.

Initial value: 60 bpm per beat; and

6) Circadian Base Rate

An alternative base rate (used instead of the aforementioned base and rest rates) set equal to the average active heart rate while the patient is awake and set equal to the average rest heart rate while the patient is at rest.

Initial value: 80 bpm active; 60 bpm rest.

The list is not necessarily exhaustive, but merely exemplary. Some of the parameters, such as the response function, the number of overdrive events and the recovery rate are unique to overdrive pacing and are used only while overdrive pacing is enabled. These parameters directly affect the degree of overdrive pacing. Other parameters are more general control parameters used by the stimulation device even when overdrive pacing is not enabled, but which can indirectly affect the degree of overdrive pacing.

At step 206, the overdrive pacing unit begins overdrive pacing the heart using the initial set of control parameters and monitors all paced and intrinsic beats over the cycle period of 24 or 48 hours. The total number of paced and intrinsic beats are recorded in memory. Upon completion of the cycle period, at step 208, the overdrive pacing unit calculates the actual degree of overdrive pacing achieved using the initial set of control parameters. The actual degree of overdrive pacing is calculated as a ratio of paced beats to total beats, i.e. paced beats divided the sum of paced and intrinsic beats, expressed herein as a percentage. Alternately, the degree of overdrive pacing may be calculated as the ratio of paced events during overdrive and recovery—exclusive, for example, of events paced at base rate, rest rate or circadian base rate—divided by the sum of all paced and intrinsic beats. The actual degree of overdrive pacing resulting from the initial set of control parameters may be, for example, 60%. At step 210, the actual degree of overdrive pacing is compared with the desired range input at step 200 and, if it is outside the range, step 212 is performed to incrementally modify one or more of the control parameters in an attempt to improve the degree of overdrive pacing. As will be explained with reference to FIG. 5, the modifications to the control parameters provided by step 212 are performed hierarchically in the order specified by the physician at step 202.

Following step 212, the overdrive pacing unit returns to step 206 to overdrive pace the heart using the modified control parameters and at the end of the next cycle period the overdrive pacing unit evaluates whether the modified control parameters have achieved the desired degree of overdrive pacing. This process is repeated until a modified set of control parameters have been found that place the actual degree of overdrive pacing within the desired range whereupon step 212 is bypassed. Instead, the overdrive pacing unit returns to step 206 to continue to pace using the same control parameters. At the completion of the next cycle period, the overdrive pacing unit again executes steps 208–210 to verify that the actual degree of overdrive pacing remains within the desired range. If, perhaps as a result of new medication taken by the patient, the actual degree of overdrive pacing begins to deviate from the desired range, further modifications are automatically made via step 212.

Thus, using the method of FIG. 4, the desired degree of overdrive pacing typically can be quickly, precisely and automatically achieved. This is in contrast to conventional techniques of the type wherein the physician manually adjusts control parameters during follow-up sessions with the patient. Hence, by using the invention, frequent follow-up sessions are typically not required and only an occasional follow-up session may be needed. In some circumstances, even after all control parameters have been modified at step 212, the actual degree of overdrive pacing still does not achieve the desired range. If so, the overdrive pacing unit suspends any further modifications and instead continues to overdrive pace using the set of parameters achieving the best degree of overdrive pacing. Eventually, during a next scheduled follow-up session, the physician reviews the final set of modified control parameters and the resulting degree of overdrive pacing and perhaps modifies the list of control parameters to be adjusted to add additional control parameters or to modify the order by which the parameters are to be adjusted. In still other cases, the physician may see fit to prescribe new or different medications. In many cases, however, the resulting degree of overdrive pacing will be sufficiently close to the desired range that the physician will be content with the set of control parameters.

Figure 1:
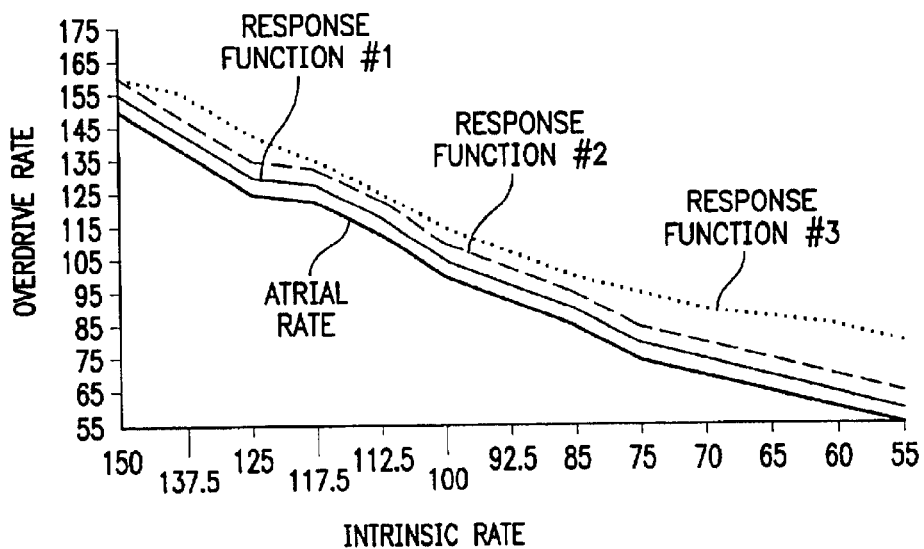
FIG. 1 is a graph illustrating a set of conventional overdrive pacing response functions used to calculate overdrive pacing rates within an implantable cardiac stimulation device.
Figure 5:
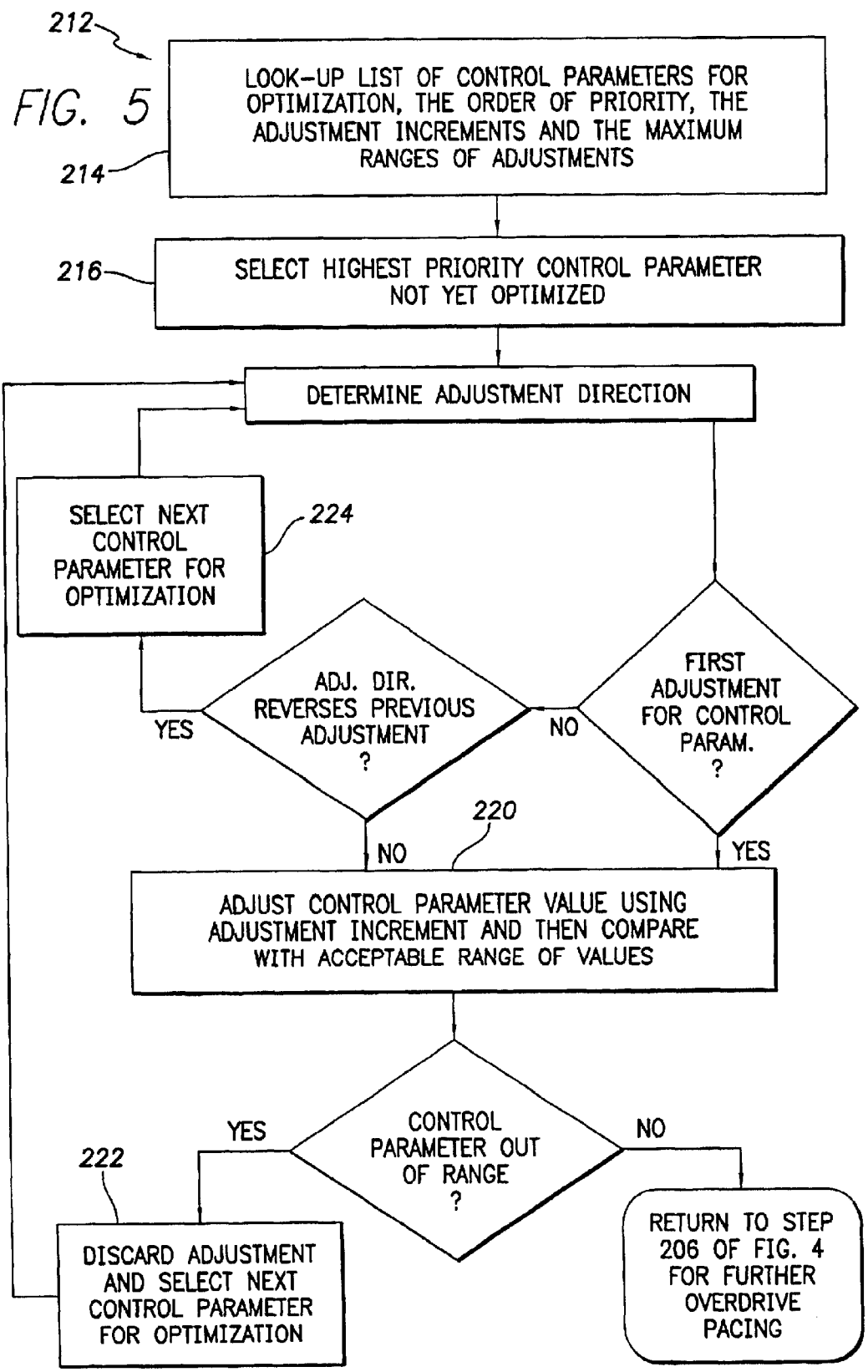
FIG. 5 is a flow chart illustrating a method for hierarchically adjusting the set of overdrive pacing control parameters of FIG. 4.

Referring now to FIG. 5, the manner by which overdrive pacing unit 103 (FIG. 3) incrementally and hierarchically modifies the control parameters within step 212 (FIG. 4) will be described. At step 214, the overdrive pacing unit looks up the list of control parameters to be optimized and the order of optimization originally input and recorded at steps 202 and 204 also (FIG. 4). Also at step 214, the increment by which each control parameter is to be adjusted and the maximum range of adjustment is also looked up. The increments and maximum ranges may be pre-stored by the manufacturer or may be specified by the physician at the time the list of control parameters for optimization is provided. For the number of overdrive events, which specifies the number of beats to pace when overdrive pacing is triggered, the adjustment increment may be set to 8 and the range may be set from 16 to 32. For the base rate, the adjustment increment may be set to 5 bpm and the range may be set from 60 to 90 bpm. For adjustment of the response function, assuming that adjustment is achieved only be selecting from among a set of fixed and substantially linear response functions, an adjustment increment is not required and the adjustment range merely encompasses the full set of predetermined response functions. An exemplary fixed set of response functions are shown in FIG. 1. For adjustment of the response function wherein a dynamic non-linear response function is employed, the adjustment increment and range relate to the amount by which break points of the response function can be adjusted and will be described in greater detail below with reference to FIGS. 6–9. For the remainder of the description of FIG. 5, it is assumed that a set of fixed and substantially linear response functions are employed and the overdrive pacing unit merely selects from among the set.

At step 216, the highest priority control parameter not yet optimized is selected for adjustment. Assuming that this is the first execution of the steps of FIG. 5, then the highest priority control parameter in the list provided by the physician is selected, for example, the number of overdrive events. At step 218, the adjustment direction for the selected control parameter is determined based on the selected control parameter and on whether the actual degree of overdrive pacing is above or below the desired range. For adjustment of the number of overdrive events, an increase results in an increase in the degree of overdrive pacing. Hence, if the actual degree of overdrive pacing is below the desired range, an increase in the number of overdrive events should increase the degree of overdrive pacing. If the actual degree of overdrive pacing is instead above the desired range, a decrease in the number of overdrive events is warranted. For adjustment of the recovery rate, an increase in the rate results in an decrease in the degree of overdrive pacing because the faster the overdrive rate recovers to the pre-overdrive rate, the sooner intrinsic beats reappear. For adjustment of the base rate, rest rate or circadian base rate, an increase in the rate usually results in an increase in the degree of overdrive pacing because intrinsic beats lower than the rate cannot occur regardless of overdrive pacing. Hence, the higher the rate, the fewer the number of intrinsic beats. For adjustment of the response function, a switch to a response function having a higher overdrive rate results in an increase in the degree of overdrive pacing. Hence, if the actual degree of overdrive pacing is below the desired range, a switch to a more aggressive response function increases the degree of overdrive pacing and vice versa.

During the first cycle of adjustment of any particular control parameter, execution proceeds from step 218 to step 220, wherein the selected control parameter (in this example the number of overdrive events) is adjusted based on the adjustment increment and direction. If the current number of overdrive events is set to 16, the increment is 8, and the adjustment direction is up, the number of overdrive events is therefore reset to 24. At step 220, the overdrive pacing unit also determines whether the adjusted value is out of range. In the example wherein the range of acceptable overdrive events is 16–32, the adjusted value of 24 is not out of range and hence execution returns to step 206 of FIG. 4 to begin overdrive pacing using the adjusted value.

Assuming the adjusted control parameter does not place the actual degree of overdrive pacing in the desired range as determined by at step 210 of FIG. 4, the steps of FIG. 5 are performed a second time. At step 216, the overdrive pacing unit again selects the number of overdrive events for optimization because the number of overdrive events has not yet been optimized, but merely adjusted. A parameter is not optimized until it either places the actual degree of overdrive pacing in the desired range or if further increments will either place the parameter out of range or will merely reverse a previous adjustment. At step 218, the adjustment direction, which may differ from the previous adjustment direction, is again calculated. The adjustment direction will differ if the adjustment took the degree of overdrive pacing from below the desired range to above the desired range or vice versa. If the adjustment direction differs from the previous direction for the same control parameter, step 224 is performed to select the next priority parameter for optimization. In this manner, the overdrive pacing unit will not repeatedly switch back and forth between two values of a control parameter which merely toggle the actual degree of overdrive pacing above and below the desired range.

Assuming, though, that the adjustment direction determined at step 218 is the same as before, step 220 is again performed to determine a new adjusted value and the adjusted value and to verified that the adjusted value is still within the acceptable range. In the example of optimization of the number of overdrive events, the value is thereby adjusted from 24 to 32 beats, still within the acceptable range. If the new adjusted value still does not place the actual degree of overdrive pacing in the desired range as determined at step 210 of FIG. 4, then upon the next execution of the steps of FIG. 5, the next adjusted value will be out of range and step 224 is instead performed to select the next control parameter out of the list for optimization. Depending upon the programming of the overdrive pacing unit, the overdrive pacing unit can reset the number of overdrive events at step 226 to the value that achieved the best degree of overdrive pacing before selecting the next parameter for optimization. For example, switching from 24 to 32 beats may have switched the degree of overdrive pacing from 84% to 98%, thus resulting in a less optimal value. Hence, it is probably better to reset the number of overdrive events back to 24 before proceeding to optimize the next control parameter. In any case, once the next control parameter is selected, the process continues to optimize that value and so on. In many cases, optimization of the first one or two control parameters is sufficient to place the degree of overdrive pacing in the desired range, hence the lower priority parameters will not be adjusted. As noted above, in some cases, optimization of all control parameters will not place the degree of overdrive pacing in the desire range. If so, the overdrive pacing unit suspends any further modifications and instead continues to overdrive pace using the set of parameters achieving the best degree of overdrive pacing.

Figure 7:
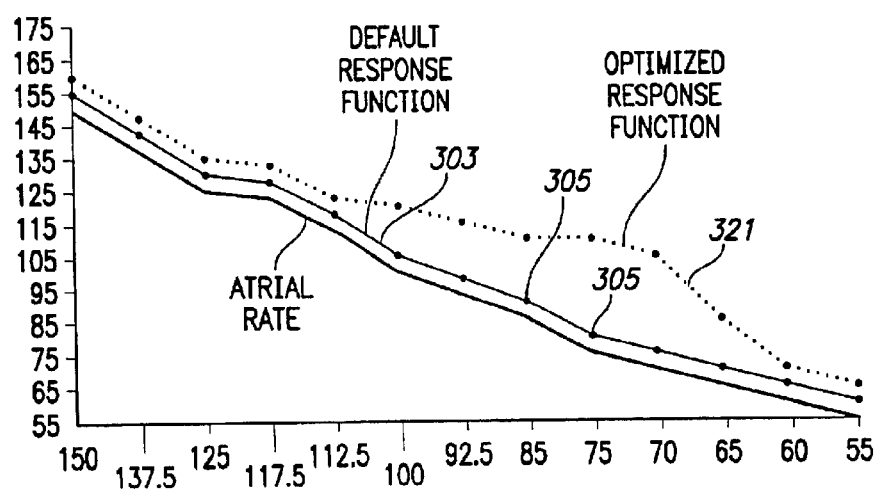
FIG. 7 is a graph illustrating the non-linear response function optimized by the method of FIG. 6.
Figure 6:
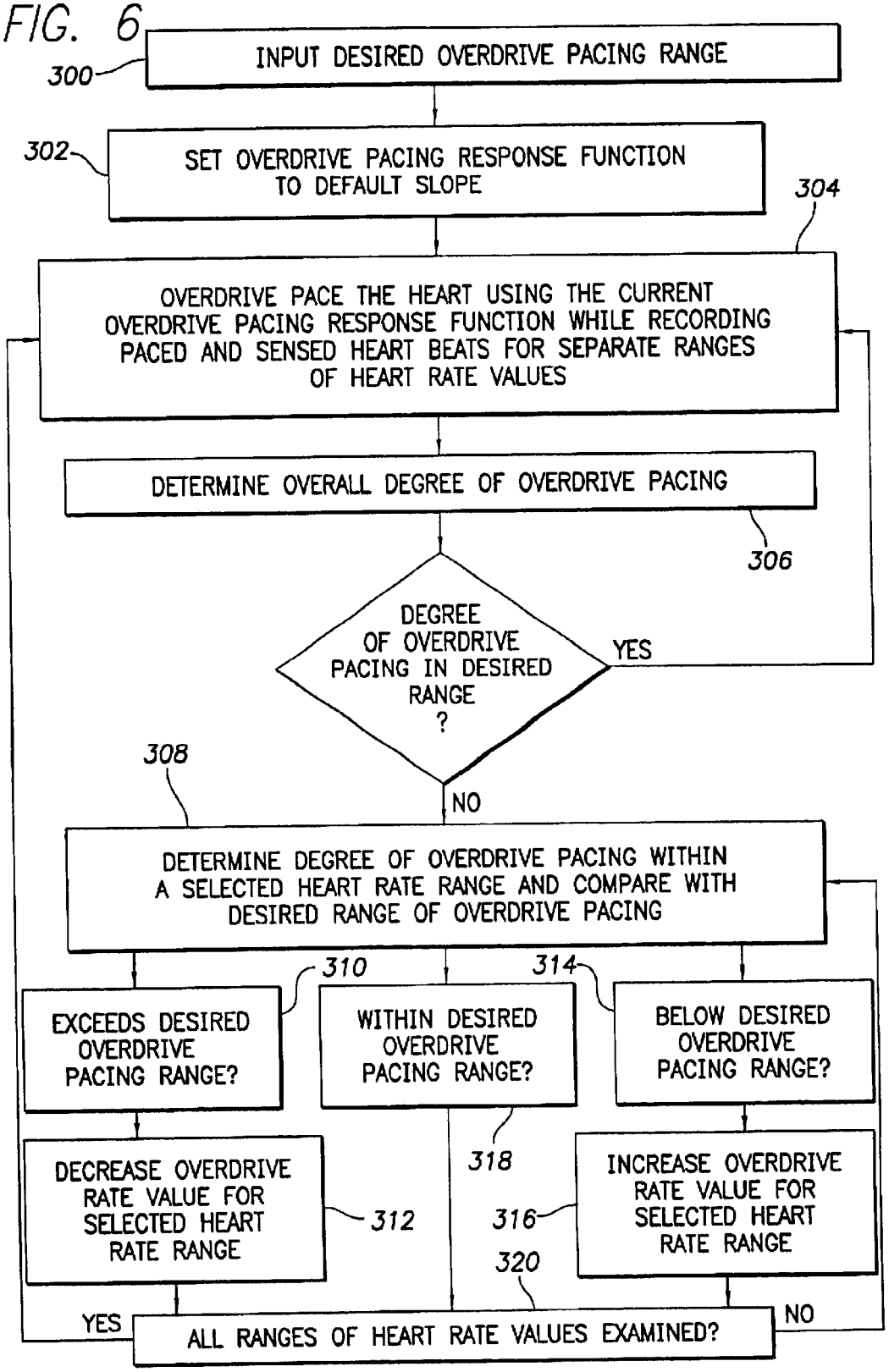
FIG. 6 is a flow chart providing an overview of the operation of a second embodiment of the invention wherein the implantable stimulation device automatically adjusts the shape of a non-linear overdrive pacing response function so as to achieve the desired degree of overdrive pacing.

What has been described thus far is a technique for hierarchically optimizing an entire set of control parameters that affect the degree of overdrive pacing. With reference to the remaining figures, a technique for optimizing a single non-linear response function will be described. FIG. 6 provides an overview the method for optimizing the single non-linear response function. Initially, at step 300, the overdrive pacing unit (FIG. 3) inputs a desired overdrive pacing range, which may be, as in the previous example, 85%–95%. At step 302, the response function to be optimized is set to a default shape or slope 303 as illustrated in FIG. 7. The shape of the response function is defined by a set of break points 305 each of which specifies an overdrive pacing rate for a particular value of the current heart rate. As one example, for a heart rate of 55, a default overdrive pacing rate of 60 is specified by a first break point. For a heart rate of 60, a default overdrive pacing rate of 65 is specified by a second break point. To determine the overdrive rate corresponding to heart rate values not specified by a particular break point, the overdrive pacing unit interpolates between the break points using any of a variety of techniques. In the example, of FIG. 7, thirteen breakpoints are provided and linear interpolation is performed between the break points. In other examples, more or fewer break points are specified. Also different interpolation schemes may be employed such as spline fits. The break points associated with lower heart rates are generally closer to one another than those of higher heart rates to provide greater precision at the lower heart rates where the actual heart rate is more likely to occur.

The set of break points defines an equal number of ranges of heart rates. The exemplary set of heart rate ranges provided by the break points of FIG. 7 are:

Range #1: 59 and below;
Range #2: 60–64;
Range #3: 65–69;
Range #4: 70–74;
Range #5: 75–84;
Range #6: 85–92;
Range #7: 92.5–99;
Range #8: 100–112;
Range #9: 112.5–117;
Range #10: 117.5–124;
Range #11: 125–137;
Range #12: 17.5–149; and
Range #13: 150 and above.

Figure 8:
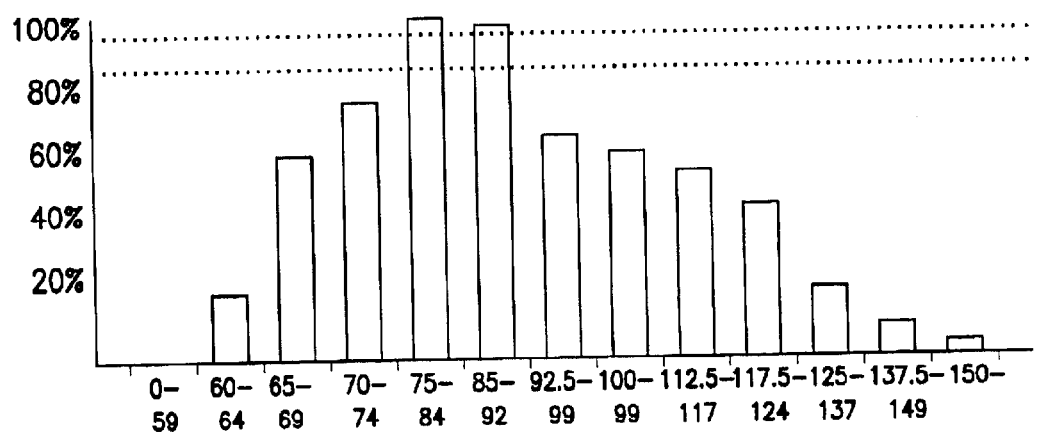
FIG. 8 is a graph illustrating an exemplary degree of overdrive pacing achieved prior to optimization of the shape of the non-linear response function of the method of FIG. 6.

At step 304, the overdrive pacing unit begins overdrive pacing the heart using the default response curve and monitors all paced and intrinsic beats over a cycle period of 24 or 48 hours. The current heart rate is monitored along with each paced and intrinsic beat. The numbers of paced and intrinsic beats for each of the set of predetermined ranges of heart rates are recorded in memory. At the end of the cycle period, at step 306, the overdrive pacing unit calculates the actual degree of overdrive pacing for each range of heart rates and calculates an overall degree of overdrive pacing. A histogram illustrating exemplary degrees of overdrive pacing for the various heart rate ranges is shown in FIG. 8 for the default response function. As shown, the default response function has resulted in a significant difference in the degree of overdrive pacing among the various the heart rate range. Moreover, the default response function has not achieved the desired degree of overdrive pacing within any of the heart rate ranges. The overall degree of overdrive pacing is therefore also not within the desired range of overdrive pacing, which is illustrated in phantom lines in the figure. Note that no beats are shown in the range of 59 beats and below because a base rate of 60 bpm has been used.

Beginning at step 308, the overdrive pacing unit begins a process to individually adjust the break points of the response function so as to modify the shape of the response function in an attempt to achieve the desired degree of overdrive pacing. To this end, at step 308, the actual degree of overdrive pacing within a selected range of heart rates is compared with the desired overdrive pacing range input at step 300. If, at step 310, the actual degree of overdrive pacing exceeds the desired overdrive pacing range, then the overdrive pacing rate of the break point of the selected range is decreased at step 312. If, at step 314, the actual degree of overdrive pacing is below the desired overdrive pacing range, then the overdrive pacing rate of the break point is increased at step 316. If, at step 318, the actual degree of overdrive pacing is in the desired overdrive pacing range, then no changes are made to the overdrive pacing rate of the break point of the selected range. Note that, at steps 312 and 316, the amount of the adjustment to the overdrive pacing rate may be a fixed, predetermined incremental amount or maybe calculated based on the magnitude of the difference between the actual degree of overdrive pacing exceeds the desired overdrive pacing range. Also, a maximum range of adjustments may be provided beyond which no further adjustments are made. For example, the overdrive rate can be constrained to remain in the range of one to thirty beats above the heart rate.

Processing then returns to step 308 via step 320 to begin examination of another range of heart rates. Once all heart rate ranges have been examined and the corresponding break point adjusted if needed, then execution instead return to step 304 via step 320 wherein the heart is overdrive paced using the adjusted response function. Upon completion of the next cycle period of 24 or 48 hours, the overdrive pacing unit again performs step 306 to calculate the actual degree of overall pacing in each of the heart rate ranges and the overall degree of overdrive pacing. If the overall degree of overdrive pacing is now within the desired range, steps 308–320 are bypassed and the overdrive pacing unit instead returns to step 306 to continue to pace using the same response function.

Figure 9:
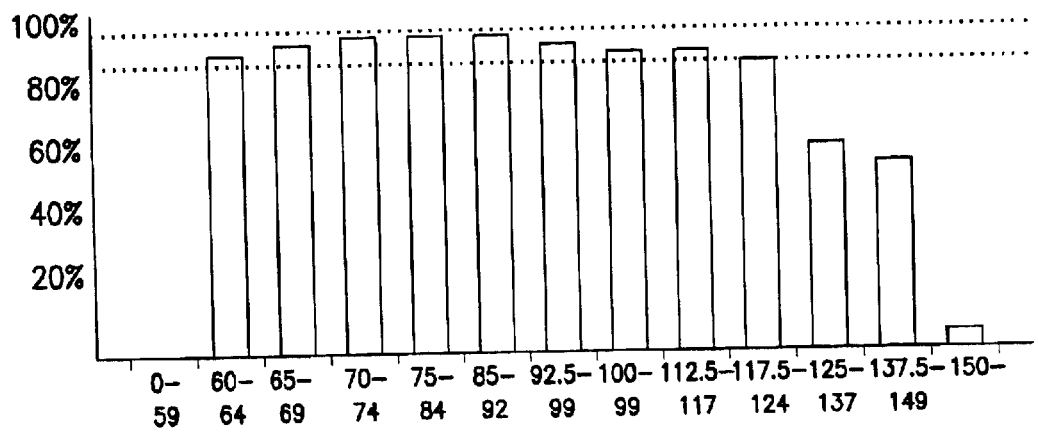
FIG. 9 is a graph illustrating an exemplary degree of overdrive pacing achieved following optimization of the shape of the non-linear response function of the method of FIG. 6.

The optimized shape of the overdrive pacing response function is shown in FIG. 7 as slope 321. A histogram illustrating exemplary degrees of overdrive pacing for the various heart rate ranges using the optimized shape of the response function is shown in FIG. 9. As shown, the adjusted shape of the response function has achieved the desired degree of overdrive pacing in most of the heart rate ranges, particularly within the lower heart rate ranges in which the heart typically beats. Although the degree of overdrive pacing in the higher ranges of heart rates are well below the optimal level, there are relatively few beats in the higher ranges and hence the overall degree of overdrive pacing is substantially unaffected.

At the completion of every cycle period, the overdrive pacing unit again performs step 306 to verify that the actual degree of overdrive pacing remains in the desired range. If the actual degree of overdrive pacing begins to deviate from the desired range, further adjustments are automatically made via steps 308–320.

Thus FIG. 7 illustrates a method by which the overdrive pacing unit iteratively adjusts the response function until the overall degree of overdrive pacing falls within a desired range. The overdrive pacing unit may be programmed with a maximum number of adjustment cycles of, for example, ten to twenty cycles, so that once the maximum number of cycles has been reached, no further adjustments are made until a physician has reviewed the results of the previous adjustments during a follow-up session with the patient. This prevents the overdrive pacing unit from continuing to make adjustments indefinitely even though the desired degree of overdrive pacing is not being achieved. The method of FIG. 7 may be used alone or in combination with the techniques of the method FIGS. 4–5.

What have been described are various techniques for automatically and dynamically adjusting parameters affecting overdrive pacing within an implantable cardiac stimulation device including adjustment of a non-linear response function. The techniques may be exploited for either atrial or ventricular overdrive pacing. If both atrial and ventricular overdrive pacing are employed, preferably separate response functions and other control parameters are maintained and independently adjusted. Also, although described primarily with reference to an example wherein the implanted device is a defibrillation/pacer, principles of the invention are applicable to other implanted cardiac stimulation devices as well such as pacemakers without defibrillation capability. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. In an implantable cardiac stimulation device having a pulse generator for generating pacing pulses for applying to a heart of a patient and having a control circuit for controlling the pulse generator to apply overdrive pacing pulses to the heart using a set of control parameters, a method, performed by the control circuit, for automatically adjusting the control parameters comprising:

acquiring an initial set of control parameters;

controlling the pulse generator, based on the set of control parameters, to overdrive pace the heart;

determining a degree of overdrive pacing achieved using the selected set of control parameters;

adjusting the set of control parameters so as to improve the degree of overdrive pacing to be achieved during further overdrive pacing;

acquiring a desired overdrive pacing range; and inputting an order of priority of control parameter adjustment and wherein adjusting the set of control parameters is performed sequentially to hierarchically adjust the control parameters in the input order of priority.

2. The method of claim 1 wherein the initial set of control parameters comprises one or more of: a number of overdrive events; an overdrive pacing response function; a recovery rate; a base rate; a rest rate; and a circadian base rate.

3. The method of claim 2 wherein the number of overdrive events specifies a number of consecutive overdrive beats to be paced following initiation of overdrive pacing.

4. The method of claim 3 wherein, if the number of overdrive events is to be adjusted, the number of overdrive events is decreased if the detected degree of overdrive pacing exceeds the desired overdrive pacing range and increased if the detected degree of overdrive pacing is below the desired overdrive pacing range.

5. In an implantable cardiac stimulation device having a pulse generator for generating pacing pulses for applying to a heart of a patient and having a control circuit for controlling the pulse generator to apply overdrive pacing pulses to the heart using a set of control parameters, a method, performed by the control circuit, for automatically adjusting the control parameters comprising:

acquiring an initial set of control parameters;

controlling the pulse generator, based on the set of control parameters, to overdrive pace the heart;

determining a degree of overdrive pacing achieved using the selected set of control parameters; and adjusting the set of control parameters so as to improve the degree of overdrive pacing to be achieved during further overdrive pacing;

acquiring a desired overdrive pacing range; and wherein adjusting the control parameters to vary the degree of overdrive pacing comprises:

selecting a control parameter to be adjusted;

comparing the degree of overdrive pacing achieved using the selected set of control parameters with the desired overdrive pacing range;

if the detected degree of overdrive pacing exceeds the desired overdrive pacing range, adjusting the selected control parameter so as to decrease the degree of overdrive pacing; and if the detected degree of overdrive pacing is below the desired overdrive pacing range, adjusting the selected control parameter so as to increase the degree of overdrive pacing; and wherein the overdrive pacing response function specifies an overdrive pacing rate to be used for overdrive pacing the heart following initiation of overdrive pacing, with the overdrive pacing rate being dependent upon detected heart rate.

6. The method of claim 5 wherein the overdrive pacing response function is selected from among a set of overdrive pacing response functions with overdrive pacing rates generally differing from one response function to another.

7. The method of claim 6 wherein, if the overdrive pacing response function is to be adjusted, an overdrive pacing response function having generally lower overdrive rates is selected if the detected degree of overdrive pacing exceeds the desired overdrive pacing range and overdrive pacing response function having generally higher overdrive rates is selected if the detected degree of overdrive pacing is below the desired overdrive pacing range.

8. The method claim 5 wherein the recovery rate specifies a rate decrement by which the overdrive pacing rate is decreased after the number of overdrive events have been paced.

9. The method of claim 8 wherein, if the recovery rate is to be adjusted, the recovery rate is increased if the detected degree of overdrive pacing exceeds the desired overdrive pacing range and decreased if the detected degree of overdrive pacing is below the desired overdrive pacing range.

10. In an implantable cardiac stimulation device having a pulse generator for generating pacing pulses for applying to a heart of a patient and having a control circuit for controlling the pulse generator to apply overdrive pacing pulses to the heart using a set of control parameters, a method, performed by the control circuit, for automatically adjusting the control parameters comprising:

acquiring an initial set control parameters;

controlling the pulse generator, based on the set of control parameters, to overdrive pace the heart;

determining a degree of overdrive pacing achieved using the selected set of control parameters;

adjusting the set of control parameters so as to improve the degree of overdrive pacing to be achieved during further overdrive pacing; and acquiring a desired overdrive pacing range;

wherein adjusting the control parameters to vary the degree of overdrive pacing comprises:

selecting a control parameter to be adjusted;

comparing the degree of overdrive pacing achieved using the selected set of control parameters with the desired overdrive pacing range;

if the detected degree of overdrive pacing exceeds the desired overdrive pacing range, adjusting the selected control parameter so as to decrease the degree of overdrive pacing; and if the detected degree of overdrive pacing is below the desired overdrive pacing range, adjusting the selected control parameter so as to increase the degree of overdrive pacing;

wherein the initial set of control parameters comprises one or more of: a number of overdrive events; an overdrive pacing response function; a recovery rate; a base rate; a rest rate; and a circadian base rate; and wherein the base rate specifies a minimum non-overdrive pacing rate for use while the patient is awake.

11. The method of claim 10 wherein, if the base rate is to be adjusted, the base rate is decreased if the detected degree of overdrive pacing exceeds the desired overdrive pacing range and increased if the detected degree of overdrive pacing is below the desired overdrive pacing range.

12. In an implantable cardiac stimulation device having a pulse generator for generating pacing pulses for applying to a heart of a patient and having a control circuit for controlling the pulse generator to apply overdrive pacing pulses to the heart using a set of control parameters, a method, performed by the control circuit, for automatically adjusting the control parameters comprising:

acquiring an initial set of control parameters;
controlling the pulse generator, based on the set of control parameters, to overdrive pace the heart;
determining a degree of overdrive pacing achieved using the selected set of control parameters;
adjusting the set of control parameters so as to improve the degree of overdrive pacing to be achieved during further overdrive pacing; and
acquiring a desired overdrive pacing range;
wherein adjusting the control parameters to vary the degree of overdrive pacing comprises:
selecting a control parameter to be adjusted;
comparing the degree of overdrive pacing achieved using the selected set of control parameters with the desired overdrive pacing range;
if the detected degree of overdrive pacing exceeds the desired overdrive pacing range adjusting the selected control parameter so as to decrease the degree of overdrive pacing; and
if the detected degree of overdrive pacing is below the desired overdrive pacing range, adjusting the selected control parameter so as to increase the degree of overdrive pacing;
wherein the initial set of control parameters comprises one or more of: a number of overdrive events; an over-drive pacing response function; a recovery rate; a base rate; a rest rate; and a circadian base rate; and
wherein rest rate specifies a minimum non-overdrive base rate for use while the patient is at profound rest.

13. The method of claim 12 wherein, if the rest rate is to be adjusted, the rest rate is decreased if the detected degree of overdrive pacing exceeds the desired overdrive pacing range and increased if the detected degree of overdrive pacing is below the desired overdrive pacing range.

14. In an implantable cardiac stimulation device having a pulse generator for generating pacing pulses for applying to a heart of a patient end having a control circuit for controlling the pulse generator to apply overdrive pacing pulses to the heart using a set of control parameters, a method, performed by the control circuit for automatically adjusting the control parameters comprising:

acquiring an initial set of control parameters;
controlling the pulse generator, based on the set of control parameters, to overdrive pace the heart;
determining a degree of overdrive pacing achieved using the selected set of control parameters;
adjusting the set of control parameters so as to improve the degree of overdrive pacing to be achieved during further overdrive pacing; and
acquiring a desired overdrive pacing range;
wherein adjusting the control parameters to vary the degree of overdrive pacing comprises:
selecting a control parameter to be adjusted;
comparing the degree of overdrive pacing achieved using the selected set of control parameters with the desired overdrive pacing range;
if the detected degree of overdrive pacing exceeds the desired overdrive pacing range, adjusting the selected control parameter so as to decrease the degree of overdrive pacing; and
if the detected degree overdrive pacing is below the desired overdrive pacing range, adjusting the selected control parameter so as to increase the degree of overdrive pacing;
wherein the initial set of control parameters comprises one or more of: a number of overdrive events; an overdrive pacing response function; a recovery rate; a base rate; a rest rate; and a circadian base rate; and
wherein circadian base rate specifies a minimum non-overdrive base rate set based on an average active heart rate while the patient is awake and based on an average rest heart rate while the patient is at rest.

15. The method of claim 14 wherein, if the circadian rate is to be adjusted, the circadian rate is decreased if the detected degree of overdrive pacing exceeds the desired overdrive pacing range and increased if the detected degree of overdrive pacing is below the desired overdrive pacing range.

16. In an implantable cardiac stimulation device having a pulse generator for generating pacing pulse for applying to a heart of a patient and having a control circuit for controlling the pulse generator to apply overdrive pacing pulses to the heart using a set of control parameters, a method, performed by the control circuit, for automatically adjusting the control parameters comprising:

acquiring an initial set of control parameters;
controlling the pulse generator, based on the set of control parameter, to overdrive pace the heart;
determining a degree of overdrive pacing achieved using the selected set of control parameters;
adjusting the set of control parameters so as to improve the degree of overdrive pacing to be achieved during further overdrive pacing;
wherein determining the degree of overdrive pacing achieved using the selected control parameters comprises:
tracking the heart rate; and
for each of a set of predetermined set of heart rate ranges, determining an overdrive pacing percentage indicative of paced heart beats to total heart beats.

17. The method of claim 16 wherein tracking the heart rate is performed over a period of 24 to 48 hours.

18. An implantable cardiac stimulation device comprising:

a pulse generator that is operative to generate pacing pulses to be applied to a heart of a patient; and
a control circuit that is operative to control the pulse generator to apply overdrive pacing pulses to the heart using a set of control parameters and for dynamically and automatically adjusting the control parameters so that a degree of overdrive pacing exceeds a predefined threshold;
wherein the control circuit comprise an overdrive pacing unit operative to input an initial set of control parameters;
control the pulse generator, based on the set of control parameters to overdrive pace the heart;
determine the degree of overdrive pacing achieved using the selected set of control parameters; and
adjust the set of control parameters so as to improve the degree of overdrive pacing to be achieved during further overdrive pacing;

wherein the overdrive pacing unit also inputs a desired overdrive pacing range;

wherein the overdrive pacing unit adjust the control parameter to vary the degree of overdrive pacing by selecting a control parameter to be adjusted, comparing the degree of overdrive pacing achieved using the selected set of control parameters with the desired overdrive pacing range, adjusting the selected control parameter so as to decrease the degree of overdrive pacing if the detected degree of overdrive pacing exceeds the desired overdrive pacing range, and adjusting the selected control parameter so as to increase the degree of overdrive pacing if the detected degree of overdrive pacing is below the desired overdrive pacing range; and wherein the overdrive pacing unit also inputs an order of priority for control parameter adjustment and adjusts the set of control parameters sequentially in the input order of priority to hierarchically adjust the control parameters.

19. The device of claim 18 wherein the initial set of control parameters input by the control circuit comprises one or more of: a number of overdrive events; an overdrive pacing response function; a recovery rate; a base rate; a rest rate; and a circadian base rate.

20. An implantable cardiac stimulation device comprising:

means for generating pacing pulses for applying to the heart of a patient;

means for acquiring an initial set of control parameters for overdrive pacing the heart;

means for controlling the means for generating pulses, based on the initial set of control parameters, to overdrive pace the heart;

means for determining the degree overdrive pacing achieved using the initial set of control parameters; and means for adjusting the initial set of control parameters so as to improve the degree of overdrive pacing to be achieve during further overdrive pacing;

wherein the means for adjusting the control parameters to vary the degree of overdrive pacing comprises:

means for selecting a control parameter to be adjusted means for comparing the degree of overdrive pacing achieved using the selected set of control parameter with the desired overdrive pacing range;

means, responsive to a determination that the detected degree of overdrive pacing exceeds the desired overdrive pacing range, for adjusting the selected control parameter so as to decrease the degree of overdrive pacing; and means, responsive to a determination that the detected degree of overdrive pacing is below the desired overdrive pacing range, for adjusting the selected control parameter so as to increase the degree of overdrive pacing.

21. In an implantable cardiac stimulation device having a pulse generator for generating pacing pulses for applying to a heart of a patient and having a control circuit for controlling the pulse generator to apply overdrive pacing pulses to the heart using a set of control parameters, a method, performed by the control circuit, for automatically adjusting the control parameters comprising:

acquiring an initial set of control parameters;

controlling the pulse generator based on the set of control parameters, to overdrive pace the heart;

determining a degree of overdrive pacing achieved using the selected set of control parameters;

inputting an order of priority of control parameter adjustment; and adjusting the set of control parameters according to the order of priority of control parameter adjustment so as to improve the degree of overdrive pacing to be achieved during further overdrive pacing;

wherein adjusting the set of control parameters is performed sequentially to hierarchically adjust the control parameters in the input order of priority.

22. In an implantable cardiac stimulation device having a pulse generator for generating pacing pulses for applying to a heart of a patient and having a control circuit for controlling the pulse generator to apply overdrive pacing pulses to the heart using a set of control parameters, a method, performed by the control circuit, for automatically adjusting the control parameters comprising:

acquiring an initial set of control parameters;

controlling the pulse generator, based; on the set of control parameters, to overdrive pace the heart;

determining a degree of overdrive pacing achieved using the selected set of control parameters; and adjusting the set of control parameters so as to improve the degree of overdrive pacing to be achieved during further overdrive pacing;

wherein the initial set of control parameters has a rest rate to specify a minimum non-overdrive base rate for use while the patient is at profound rest; and wherein, if the rest rate is to be adjusted, the rest rate is decreased if the detected degree of overdrive pacing exceeds the desired overdrive pacing range and increased if the detected degree of overdrive pacing is below the desired overdrive pacing range.

23. In an implantable cardiac stimulation device having a pulse generator for generating pacing pulses for applying to a heart of a patient and having a control circuit for controlling the pulse generator to apply overdrive pacing pulses to the heart using a set of control parameters, a method, performed by the control circuit, for automatically adjusting the control parameter comprising:

acquiring an initial set of control parameters;

controlling the pulse generator, based on the set of control parameters, to overdrive pace the heart;

determining a degree of overdrive pacing achieved using the selected set of control parameters; and adjusting the set of control parameters so as to improve the degree of overdrive pacing to be achieved during further overdrive pacing;

wherein the initial set of control parameters has a circadian base rate to specify a minimum non-overdrive base rate set based on an average active heart rate while the patient is awake and based on an average rest heart rate while the patient is at rest.

24. An implantable cardiac stimulation device comprising:

a pulse generator that is operative to generate pacing pulses to be applied to a heart of a patient;

a control circuit that is operative to control the pulse generator to apply overdrive pacing pulses to the heart using a set of control parameters and for dynamically and automatically adjusting the control parameters so that a degree of overdrive pacing exceeds a predefined threshold; and an overdrive pacing unit to input an order of priority for control parameter adjustment and to adjust the set of control parameters sequentially in the input order of priority to hierarchically adjust the control parameters.

* * * * *